United States Patent [19]
Carlson

[11] Patent Number: 5,700,428
[45] Date of Patent: Dec. 23, 1997

[54] FLUORESCENCE DETECTOR, AND A DEVICE FOR SUPPORTING A REPLACABLE SAMPLE CUVETTE IN A FLUORESCENCE DETECTOR

[75] Inventor: Leon Carlson, Täby, Sweden

[73] Assignee: CMA/Microdialuysis Research AB, Stockholm, Sweden

[21] Appl. No.: 569,259

[22] PCT Filed: Jun. 21, 1994

[86] PCT No.: PCT/SE94/00615

§ 371 Date: Dec. 22, 1995

§ 102(e) Date: Dec. 22, 1995

[87] PCT Pub. No.: WO95/00832

PCT Pub. Date: Jan. 5, 1995

[30] Foreign Application Priority Data

Jun. 24, 1993 [SE] Sweden .................. 9302193

[51] Int. Cl.$^6$ .................................................. G01N 21/64
[52] U.S. Cl. ............................. 422/82.08; 422/82.11; 250/368; 250/461.1
[58] Field of Search ............ 436/172; 422/82.06, 422/82.07, 82.08, 82.11; 250/361 R, 365, 368, 461.1, 461.2, 363.01

[56] References Cited

U.S. PATENT DOCUMENTS

| 5,304,492 | 4/1994 | Klinkhammer | 436/172 X |
| 5,460,943 | 10/1995 | Hayashi et al. | 436/172 X |

FOREIGN PATENT DOCUMENTS

| 170998 | 9/1992 | Norway . |
| 2 215 838 | 9/1989 | United Kingdom . |
| 9214137 | 8/1992 | WIPO . |

*Primary Examiner*—Jeffrey Snay
*Attorney, Agent, or Firm*—Young & Thompson

[57] ABSTRACT

A fluorescence detector has a light source in the form of a halogen lamp, a UV-filter which allows excitation radiation in UV to pass through, and a second filter which sorts out fluorescence radiation, and a detector which detects the through-passing fluorescence radiation. The filters comprise thin straight blocks and also function as light guides and are positioned at right angles with their extensions directed towards a point at which a tubular sample can be placed in close with the ends of the filters distal from the light source and the detector.

13 Claims, 2 Drawing Sheets

FLUORESCENCE DETECTOR, AND A DEVICE FOR SUPPORTING A REPLACABLE SAMPLE CUVETTE IN A FLUORESCENCE DETECTOR

FIELD OF THE INVENTION

The present invention relates to a fluorescence detector for measuring fluorescence in a liquid contained in a tube, comprising a light source for irradiating the liquid with fluorescence-generating radiation, a filter through which fluorescence radiation emitted by the liquid passes, and a detector which functions to detect fluorescence radiation that has passed through the filter and to produce an electric signal corresponding to said fluorescence radiation.

The invention also relates to a carrier device for a cuvette intended for simple, reproducible replacement in a fluorescence detector.

BACKGROUND OF THE INVENTION

Many different makes of apparatus for activating and detecting fluorescence radiation from liquids are commercially available. The liquid is introduced into a cuvette or is allowed to flow past a measuring point, where it is irradiated with UV-light from a light source, while resultant fluorescence radiation is sorted out and passed to an intensity measuring detector. In many instances monochromators are used both for producing radiation and for sorting out fluorescence radiation of a given wave-length. Although it is possible to manufacture such instruments with a high degree of sensitivity and therewith allow The detection of small concentrations, such instruments are unavoidably very expensive. Simpler instruments which operate solely with colour filters are also available, although these instruments are not able to satisfy the same high requirements at present.

SUMMARY OF THE INVENTION

An object of the present invention is to provide a fluorescence detector which is simple and inexpensive in manufacture but which, nevertheless, will provide high detection sensitivity. The detector is primarily intended to be used with through-flowing samples from small chromatography columns or in so-called flow injection systems, although it can also be used with static samples. In the case of the applications for which the invention is primarily intended, it is possible to use relatively broad wavelength bands for both the incident exciting radiation and the captured emitted radiation. This is possible because of the high degree of sensitivity that can be obtained due to the effective use of the light, and because it is possible to use colour filters in the majority of cases, provided that these filters are suitably constructed.

Another object of the invention is to provide a simple and practical exchange possibility for cuvettes and samples mounted in exchangeable cassettes.

These and other objects of the invention are achieved in accordance with the invention with a fluorescence detector having the characteristic features set forth in the claims.

One particularly distinguishing feature of one embodiment of the invention is that the filters used have the form of plates cut from filter material and fulfill two different functions simultaneously, namely a filter function and a light conducting function. In this way, there is achieved both a good filter effect for long wavelengths through the filters and favourable collimation, despite the fact that no lenses are required. However, the filter effect can also be achieved by placing separate filters in the beam paths.

With regard to the carrier device or the cassette according to the invention, one characteristic feature resides in the use of an inner corner in the detector, in the form of a surface from which fluorescence exciting light is emitted towards a cuvette or the like, and a surface which is angled in relation to the first-mentioned surface and through which fluorescence light is taken up for detection, wherein the cuvette or like device is mounted resiliently in the cassette and is pressed in towards the two surfaces to take a fully reproducible position when mounting the cassette.

Similar to known fluorescence detectors, there is used a sample cuvette which consists in a thin tube of transparent material, preferably quartz, through which the examined liquid flows. The quartz tube is mounted advantageously so as to abut the short sides of the two filters. Particularly when the tube and associated connections are mounted in a replaceable or exchangeable cassette, an advantage is obtained when the cassette includes resilient means which, when the cassette is fitted, resiliently press the outer wall surface of the tube against the short sides of the tube filters, said filters preferably being mounted in a holder having an inner corner angled at 90 degrees.

BRIEF DESCRIPTION OF THE DRAWINGS

The invention will now be described in more detail with reference to non-limiting exemplifying embodiments thereof and also with reference to the accompanying drawings, in which.

DETAILED DESCRIPTION OF THE INVENTION

Figure 1:
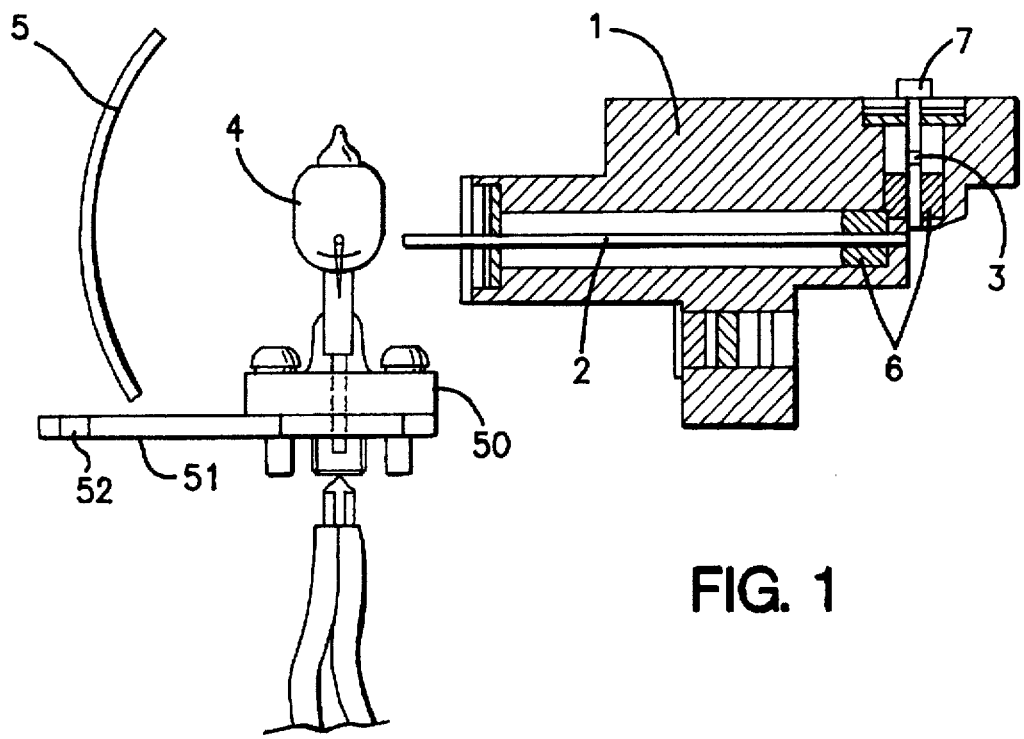
FIG. 1 is a sectioned view of a fluorescence detector constructed in accordance with the principles of the invention, with no sample mounted.

FIG. 1 illustrates a fluorescence detector in accordance with one exemplifying embodiment, the detector being shown in twice its natural size. Mounted in a holder 1 of solid black plastic at right angles to each other are a first light conductor 2 which also functions as a filter which is permeable to ultra-violet light, and a second light conductor 3 which also functions as a filter which is permeable to fluorescence light, wherein the two light conductors meet at their respective one ends to form an inner corner. A bulb 4 is mounted at the distal short end of the first light conductor, while a detector unit 7 is seated on the distal short end of the second light conductor. These two filters, which have the form of a right-angled block, are rigidly attached in the holder 1, with light-impervious, black thermosetting resin 6 (preferably silicone rubber) surrounding said meeting ends, so that only the their short-side surfaces are exposed. The end of the light conductor/filter 2 that lies proximal to the bulb 4 projects slightly out from the holder 1 and a portion of said projecting part extends into the bulb housing. The bulb 4 is mounted in a lamp housing (not shown) and is there ventilated by a fan, which also functions to cool that part of the filter which protrudes from the holder 1. As a result, only a small amount of heat is conducted to the sample. A reflector 5 may optionally be placed behind the bulb 4. The detector 7 will preferably be a photodiode whose sensitive surface is placed towards the short side of the light conductor 3 and an intermediate plastic filter is provided to eliminate any transmitted UV-radiation that may have successfully passed through the filter effect of the light conductor 3.

Figure 2:
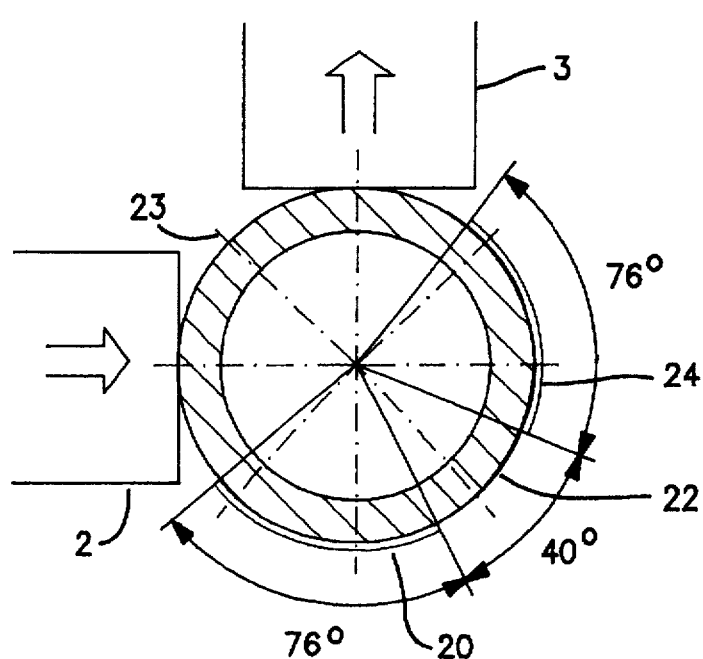
FIG. 2 is an enlarged view of a sample position and shows a quartz tube in cross-section and a radiation delivering and fluorescence radiation collecting optical element to those parts that are close to the sample.

FIG. 2 illustrates schematically the corner formed by the two light guides 2 and 3, this view being enlarged 35 times, and a quartz tube 10 fitted therein through which or in which a liquid sample can be passed or stored respectively. Fluorescence-generating excitation radiation arrives in the direction of the arrow towards the tube and generates therein fluorescence radiation, provided that the liquid contained in the tube fluoresces. Part of this fluorescence exits from the tube and enters the light guide 3, where it is filtered to eliminate any UV-radiation that may have been diverted in this direction, by dispersion, reflection or refraction. The actual tube 10 will preferably be free from fluorescence, and consequently the tube is normally made of quartz.

In order to increase intensify, the tube 10 may be provided partially with a reflective coating on its outer surface, preferably an aluminum coating. FIG. 2 illustrates the preferred application of the reflective coatings 20 and 21, each covering 76 degrees with an interspace 22 of 40 degrees. It will be understood that these values are proposed values and thus not critical. It is important, however, that there is found an intermediate space in a field around the location of the bisector 23 between the pupil surfaces of the light conductors 2 and 3, so as to prevent the excitation radiation being directed towards the outlet pupil to any great extent, via reflection.

The radiation geometry has therewith been shown in cross-section. This cross-section is representative of the geometry that prevails over a given length of the tube 10, which considerably exceeds the cross-sectional dimensions shown in FIGS. 1 and 2. These illustrated cross-sections are sections through the thickness of the light conductors/filters 2 and 3, which have the form of elongated plates with their largest extension and their smallest extension shown in FIG. 1.

It will be noted that although it is normally preferred to use cylindrical tubes, it is also possible to use cuvettes and tubes of other shapes when this is practical for some reason or another. It is thus obvious that a tube of square cross-section can be fitted in the same optical system without detriment.

Figure 3:
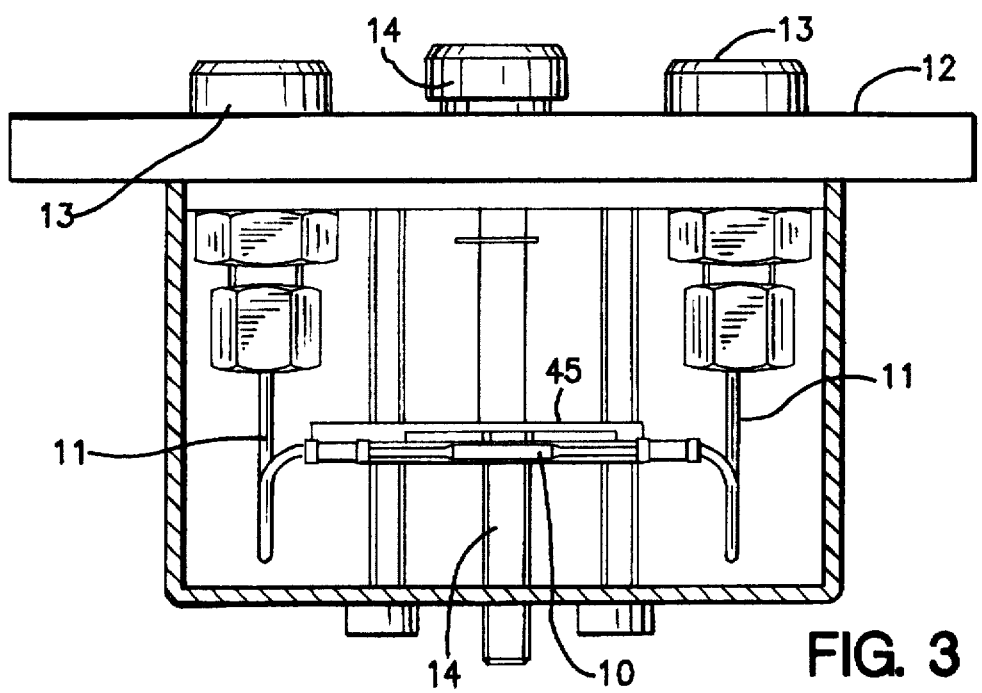
FIG. 3 illustrates a cassette having a resiliently mounted quartz sample-tube.

The tube 10 is thus mounted at the point of intersection of the optical light conductors 2 and 3, as shown in FIG. 2. According to this preferred embodiment, the tube 10 is replaceably mounted in a cassette, such as via flexible and resilient steel pipes 11 in a cassette 12 according to FIG. 3. The holder 1 shown in FIG. 1 is mounted together with a cooled lamp housing in a casing in a manner not shown, said casing having an opening into which the cassette 12 can be slid, in the manner of a sliding box. The cassette 12 is secured by means of a screw 14 after having been slid into the opening. The tube 10 then extends obliquely from beneath towards the inner corner in FIG. 1 and is held in resilient contact by the flexible stainless pipes 11.

Figure 4:
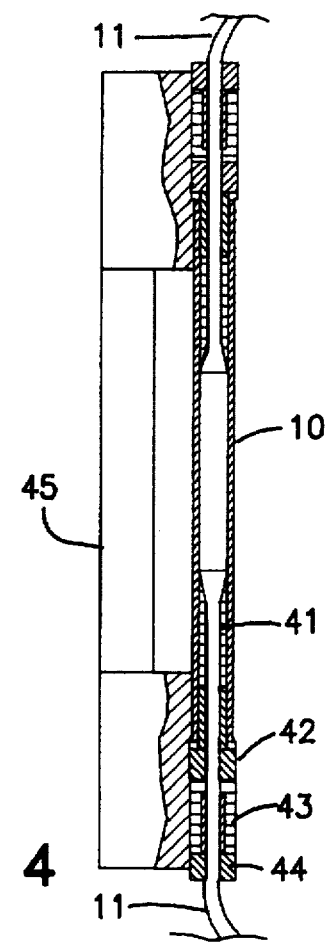
FIG. 4 is a longitudinal sectioned view of a quartz sample tube.

FIG. 4 illustrates how the tube 10 is sealingly connected to the steel pipes 11. In this regard, the pipes 11 are collared so as to provide a close fit with the inner surface of the tube 10, and a pipe 41 made of plastic-elastic material, for instance FEP, is fitted, followed by an apertured plug. The plug 42 pushes against the pipe 41 therewith causing the pipe to deform and seal in the space between the inner surface of the tube 10 and the outer surface of the steel pipe 11, and is loaded with a spring 43 tensioned with a further apertured plug 44 which is held in place by the tension of the pressure spring 43, by virtue of a bend in the pipe 11. As will be seen from FIG. 3, the pipes 11 are then curved, so that the tube 10 is kept free between connections 13, which permit connection to a liquid source, for instance a chromatographic column. When a quartz tube is used, it is convenient to provide on one side opposite to the tube abutment side a reinforcing bar which joins the pipes 11 to the joins.

The light source used in the illustrated case is a halogen lamp 4 which is mounted in a jig 50 comprising a plate 51 provided with a hole 52 for reproducible mounting. An electrical connector is provided with electrical connections. In the described embodiment, there is used a 12V, 20 W bulb (model Q20 G4) with the filament extending parallel with the entry surface of the first filter 2 and with the axial direction of the tube 10.

It has been found that for normal requirements, it is sufficient to provide a stabilized d.c. voltage for supplying the bulb with energy, i.e. so as to obtain good long term stability over a test period, including any calibration necessary. As will be made apparent below, it is also possible to monitor the intensity by means of a two-beam device.

Figure 5:
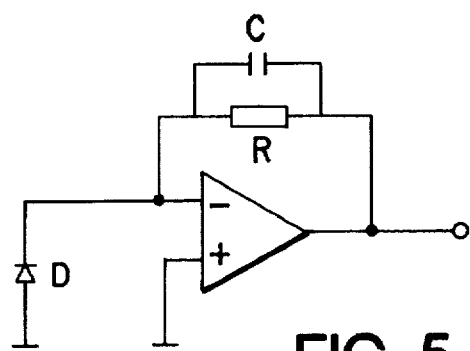
FIG. 5 illustrates an electric circuit of a photodiode with preamplifier.

The detector used is suitably a photodiode, which is beneficial in view of the fact that it has good linearity over a large dynamic range (4–5 powers of ten). As illustrated schematically in FIG. 5, the light-quanta-generated current is passed through a high-resistive resistor (10 Gohm) and the signal obtained is amplified in a preamplifier. The resistor and the amplifier are positioned in the close proximity of the photodiode and are well screened. The amplified signal is preferably led to a voltage/frequency converter, this being suitable as the operations concerned are relatively slow. The diode used is a photodiode. A Hamamatsu photodiode, model designation S 2387-16, was used in one construction.

The combined light conductors and filters are suitably manufactured by cutting commercially available glass filter plates into strips, these plates often being available in square shapes having a thickness of 1 mm, for instance. A width of about 10 mm is appropriate, and the length will preferably be much greater than the thickness, particularly in the case of the UV-filter, which will preferably be at least 10 times longer, preferably at least 50 times longer than the thickness, whereas the intake filter will be at least 6 times longer, preferably at least 10 times longer than the thickness. The cut edge surfaces of the filter strips cut from said plates are ground and polished, without any particular optical tolerance requirements. Suitable filters can have a pass band, the UV-filter somewhere between 300 and 380 nm, the second filter between 400 and 500 nm, although special requirements can be satisfied by individual adaptation of the filters. The best length of the filters is determined in view of the type of filter used.

In one constructed example of a fluorescence detector, there was used a quartz tube which had an outer diameter of 1.5 mm and an inner diameter of 1.1 mm. The thickness of the filter glass used was 1 mm. The UV-filter was made by Schott, type UG5 (pass band 310–350 nm) and measured 49×6×1 mm. The second filter, also a Schott make, type BG 39 (pass band 410–480 nm), measured 12×6×1 mm. The end of the detector was supplemented with a small plastic filter impervious to UV (non-transparent under 390 nm, type KV 389 from Schott).

Comparisons have been made with commercially available fluorescence detectors. It was found that with an irradiated cell volume of 5.7 µl, the detection limit of the standard substance quinine sulphate was 0.010 pg/µl (with the detection limit defined as a signal level reaching to twice the background noise). Sensitivity is therewith essentially on a level with what, according to available data sheets, is said to have been achieved with the best of the tested instruments generally available commercially.

Figure 6:
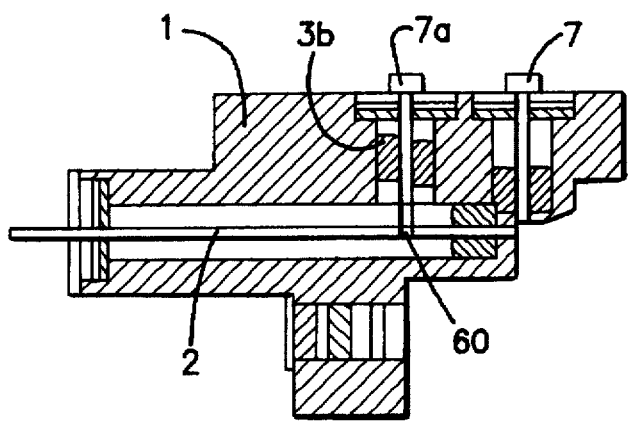
FIG. 6 illustrates a variant of the embodiment shown in FIG. 1 in which a normalizing device of the two-beam type is arranged.

As before mentioned, it has been found that the use of a single-beam system in accordance with what has already been described is generally sufficient for illumination. However, if particularly high requirements are placed on the stability and reproduceability of the measuring process, there can be provided a reference system for measuring the radiation emitted from the bulb, for instance in accordance with FIG. 6, where like details have been identified with like reference signs. There has been drilled in the light conductor 2 a hole 60 which takes-up a small part of its width (less than 10–15%). This hole has placed therein, for instance by embedment, a plug of fluorescent material which when impinged upon by the radiation led through the light conductor emits fluorescence radiation of which a part is captured by a light conductor 3b and led to a reference photodiode 7b, which thus detects a signal that is a measure of the excitation radiation. This enables the following advantages to be achieved:

Because part of the luminescence that passes towards the measuring cuvette is taken-out as a reference, the measured light and the reference light are both taken from the same part of the light source and in the same direction.

Because the reference beam has passed through a substantial length of the light conductor 2, the reference beam will have generally the same spectral composition as the excitation beam that impinges on the sample when the reference beam strikes the reference plug, provided that the light conductor has a filtering effect. In addition, if the light conductor 2 has a filtering effect, the fluorescence radiation generated by the plug will be absorbed as a result of the position of the plug before the radiation can reach the sample, therewith scarcely influencing the background.

The reference plug can be produced from a fluorescent material whose fluorescence properties are similar to those exhibited by samples to be analyzed.

Because the photodiodes 7 and 7b have been placed close together and mechanically mounted in similar ways, several advantages are achieved, for instance the photodiodes can be connected electrically to the same circuit board on which the two amplifiers are mounted, and the two photo-diodes can be readily held at the same temperature.

The plug may be replaced with a mirror positioned at 45 degrees, a total reflecting prism or some light-spreading device, to transmit part of the excitation light through the light guide 3b. In this regard, the property according to the latter point is not relevant and in this case, it is necessary to produce the light guide 3b from a material which will allow the excitation light to pass through.

I claim:

1. In a fluorescence detector for measuring fluorescence in a liquid comprising a light source for irradiating the liquid with fluorescence generating radiation, a filter for allowing fluorescence radiation generated by liquid to pass through, and a detector for detecting fluorescence radiation that has passed through the filter and for producing an electric signal corresponding to the fluorescence radiation, the improvement comprising:

an elongated, flat-shaped first light conductor having a first end in proximity to the light source, and a second end adapted to be positioned in proximity to an irradiated region of a liquid-containing tube having an inner diameter approximating the thickness of the first light conductor, said first light conductor having a length which is at least 10 times said thickness, and functioning as a filter to provide a first filter effect which is pervious to ultraviolet light but impervious to wavelength ranges of generated fluorescence radiation;

an elongated, flat-shaped second light conductor having a first short side in proximity to the detector, and a second short side adapted to be positioned in proximity to a detection region of the tube whose inner diameter approximates the thickness of the second light conductor, said second light conductor having a length which is at least 6 times that of its thickness, said second light conductor being pervious to fluorescence radiation and functioning as a filter to provide a second filter effect;

wherein the light conductors are positioned with their longitudinal axes in mutual transverse directions, and wherein in use, the second end of the first light conductor and the second short side terminate almost tangentially with the outer surface of the tube, and the irradiated region and the detection region coincide at least partially in the longitudinal direction of the tube.

2. A fluorescence detector according to claim 1, further comprising an exchangeable cassette for mounting the tube therein.

3. A fluorescence detector according to claim 1, wherein the light source is a halogen bulb contained in a quartz casing.

4. A fluorescence detector according to claim 1, wherein the detector is a photodiode.

5. A fluorescence detector according to claim 1, wherein the outer surface of the tube is coated partially with a reflective layer, which in use leaves exposed a surface of the tube that is located at a region around a bisector between the two surfaces of the light conductors that are closest to the tube.

6. A fluorescence detector according to claim 1, wherein the filter effects of the light conductors are achieved by producing the light conductors from filter material.

7. A fluorescence detector according to claim 6, further comprising a reference system which includes a fluorescent reference sample mounted in the first light conductor between the first end and second end, a third light conductor having one end directed towards the reference sample, and an intensity monitoring second detector arranged at an opposite end of said third light guide.

8. A fluorescence detector according to claim 1, further including means for pressing the tube resiliently against the light guides.

9. A fluorescence detector according to claim 8, wherein metal inlet and outlet pipes having collared ends are inserted into both ends of the tube, followed by tubular members which are made of a deformable plastic material and fitted over the inserted metal pipes, and plug means which are made of a harder material and are press-fitted into the tube, said plug means being resiliently pressed against the fitted tubular members.

10. A fluorescence detector according to claim 1, wherein the first filter effect has a pass band of between 310–350 nm, and the second filter effect has a pass band between 410–480 nm.

11. A fluorescence detector according to claim 10, wherein the second filter effect is combined with a plastic UV-filter.

12. A fluorescence detector according to claim 1, further comprising a cuvette in the fluorescence detector, means for fitting the carrier device and an attachment end thereof to the fluorescence detector in a specific mounting position, wherein the cuvette is suspended from the carrier device via resilient inlet and outlet lines, so that after fitting the carrier device to the fluorescence detector, the cuvette is pressed by support surfaces provided in the fluorescence detector from a first position to a second measuring position which can be reproducibly well-defined in relation to the fluorescence detector and its support surfaces.

13. A fluorescence detector according to claim 12, wherein the cuvette is made of quartz glass and is reinforcingly supported between the inlet and outlet lines by a bar which joins said lines on one side of the cuvette that lies distal from the support surfaces of the fluorescence detector.

* * * * *